United States Patent
Honert et al.

(10) Patent No.: US 10,214,472 B2
(45) Date of Patent: Feb. 26, 2019

(54) STABILIZATION OF CRUDE POLYOLS FROM BIOMASS

(71) Applicant: SIKA TECHNOLOGY AG, Baar (CH)

(72) Inventors: Dieter Honert, Dielheim (DE); Hans Knauber, Eppelheim (DE); Thomas Müller, Heidelberg (DE)

(73) Assignee: SIKA TECHNOLOGY AG, Baar (CH)

( * ) Notice: Subject to any disclaimer, the term of this patent is extended or adjusted under 35 U.S.C. 154(b) by 943 days.

(21) Appl. No.: 14/355,047

(22) PCT Filed: Dec. 6, 2012

(86) PCT No.: PCT/EP2012/074640
§ 371 (c)(1),
(2) Date: Apr. 29, 2014

(87) PCT Pub. No.: WO2013/083692
PCT Pub. Date: Jun. 13, 2013

(65) Prior Publication Data
US 2014/0299022 A1    Oct. 9, 2014

(30) Foreign Application Priority Data

Dec. 6, 2011 (EP) .................................. 11192123

(51) Int. Cl.
| | |
|---|---|
| *C07C 29/94* | (2006.01) |
| *C04B 7/52* | (2006.01) |
| *C04B 24/02* | (2006.01) |
| *C04B 28/02* | (2006.01) |
| *C04B 40/00* | (2006.01) |
| C04B 103/52 | (2006.01) |

(52) U.S. Cl.
CPC ................. *C07C 29/94* (2013.01); *C04B 7/52* (2013.01); *C04B 24/02* (2013.01); *C04B 28/02* (2013.01); *C04B 40/0039* (2013.01); *C04B 2103/52* (2013.01)

(58) Field of Classification Search
CPC ......... C07C 29/94; C04B 24/02; C04B 28/02; C04B 7/52
See application file for complete search history.

(56) References Cited

U.S. PATENT DOCUMENTS

| | | | | |
|---|---|---|---|---|
| 5,938,835 | A * | 8/1999 | Shawl | C04B 24/023 |
| | | | | 106/724 |
| 7,108,800 | B2 * | 9/2006 | Tran | C09K 3/22 |
| | | | | 241/16 |
| 7,922,811 | B2 * | 4/2011 | Jardine | B02C 23/06 |
| | | | | 106/823 |
| 2006/0004148 | A1 | 1/2006 | Sulser et al. | |
| 2006/0272554 | A1 | 12/2006 | Jardine et al. | |
| 2008/0119602 | A1 | 5/2008 | Sulser et al. | |
| 2008/0227890 | A1 | 9/2008 | Maeder et al. | |
| 2009/0078163 | A1 | 3/2009 | Rossi et al. | |
| 2009/0227709 | A1 | 9/2009 | Maeder et al. | |
| 2011/0146540 | A1 | 6/2011 | Jardine et al. | |
| 2012/0270972 | A1 | 10/2012 | Maeder et al. | |

FOREIGN PATENT DOCUMENTS

| | | |
|---|---|---|
| CN | 101125742 A | 2/2008 |
| EP | 1 348 729 A1 | 10/2003 |
| EP | 1 138 697 B1 | 11/2003 |
| EP | 1 061 089 B1 | 3/2004 |
| JP | 10167786 * | 6/1998 |
| WO | 01/12581 A1 | 2/2001 |
| WO | WO 2005/123621 A1 | 12/2005 |
| WO | WO 2006/051574 A2 | 5/2006 |
| WO | WO 2006/132762 A2 | 12/2006 |
| WO | WO 2010/062484 A1 | 6/2010 |

OTHER PUBLICATIONS

International Search Report issued in International Application No. PCT/EP2012/074640 dated May 21, 2013.
International Preliminary Report on Patentability issued in International Application No. PCT/EP2012/074640 dated Jun. 10, 2014.
Apr. 13, 2018 Offce Action issued in European Application No. 12797913.6.

* cited by examiner

*Primary Examiner* — Shuangyi Abu Ali
(74) *Attorney, Agent, or Firm* — Oliff PLC

(57) ABSTRACT

A solubilizer is used to stabilize crude polyol produced from biomass.

17 Claims, No Drawings

STABILIZATION OF CRUDE POLYOLS FROM BIOMASS

TECHNICAL FIELD

The invention relates to the stabilization of crude polyols produced from biomass. Furthermore, the invention relates to a composition containing a crude polyol produced from biomass as well as a method of grinding a solid.

PRIOR ART

A central step and major cost factor in the production of mineral binders, especially cement, is the grinding of the coarse-grained mineral components into a fine powder. Thus, during cement production for example, clinkers and optionally other additives depending on the type of cement, such as foundry sand or limestone, are ground into a fine powder. The cement and the additives can basically be ground up together or also separately.

The fineness of the mineral binder or the additives is an important quality feature here. For example, hardened mortar or concrete blends with finely ground mineral binders generally have higher compressive strength than the corresponding blends based on more coarsely ground mineral binders.

In order to facilitate the comminution of mineral binders or additives in grinding mills and hinder the agglomeration of the resulting powderlike particles, so-called grinding adjuvants are used. These bring about a strong reduction of the grinding time and the energy expenditure needed for the grinding. Grinding adjuvants are added along with the grinding material in the cement mill in quantities of up to around 0.2%, in exceptional instances up to 0.5%, depending on the grinding material. This can increase the mill throughput performance by 20 to 30%, in some systems even up to 50%, for the same fineness or identical Blaine's value of the binder.

Organic liquids have proven themselves as grinding adjuvants since the 60s, especially glycols and amino alcohols. The use of glycerin as a grinding adjuvant is also known.

WO 2006/132762 A2 (W.R. Grace & Co.—Conn.) discloses in this regard for example the use of polyols from biomass. For example, crude glycerin, which comes about as a by-product of the production of biodiesel, among other things, is used in grinding adjuvant compositions. As compared to glycerin from fossil sources, the grinding efficiency can be improved with biomass-based polyols. Furthermore, glycerin from biomass is advantageous in ecological respect.

However, when polyols from biomass are used as part of grinding adjuvant compositions, especially crude glycerin, there is often fouling of pumps and pipelines, as well as disruptions during the grinding of solids or binders. Furthermore, one also has to deal with resinification effects.

PRESENTATION OF THE INVENTION

The problem of the present invention is therefore to make available crude polyols from biomass, especially crude glycerin, having few or none of the aforementioned drawbacks. In particular, the crude polyols should be capable of being used as grinding adjuvants or in grinding adjuvant compositions and should facilitate or improve the grinding process of inorganic and/or mineral solids, especially mineral binders. Moreover, a corresponding composition should be provided that can be used advantageously as a grinding adjuvant.

The problems are solved according to the invention by the features of the independent claims.

Accordingly, the heart of the invention is the use of a solubilizer to stabilize crude polyol produced from biomass.

As has been shown, crude polyols from biomass contain oily components as secondary components due to the production process. For example, crude glycerin from the production of biodiesel typically contains a fraction of rapeseed oil or methyl ester of rapeseed oil. These oily secondary components are poorly soluble in the crude polyols, such as crude glycerin, or in aqueous mixtures of crude polyols, and have a tendency to separate. Therefore, after only a short time undesirable separation phases already occur on the surface of the crude polyols or the crude glycerin, which leads to the aforementioned drawbacks, among others.

However, with the help of the solubilizer according to the invention, especially an alkaline substance, it is possible to achieve a stabilization of the crude polyols from biomass. It has been found that the crude polyols from biomass remain stable for a long time thanks to the solubilizer, and an unwanted phase separation can be greatly reduced or even totally prevented. Thus, the crude polyols from biomass are present in the form of a stable and essentially homogeneous phase.

When the crude polyols from biomass which are so treated are used as grinding adjuvants, one can greatly reduce fouling of pumps and pipelines, as well as disruptions during the grinding of solids or binders. Resinification effects also diminish significantly.

Furthermore, it has been found that the solubilizer has little or no negative impact on the grinding process itself or the properties of the ground product.

Other aspects of the invention are the subject of further independent claims. Especially preferred embodiments of the invention are the subject of the dependent claims.

WAYS OF IMPLEMENTING THE INVENTION

A first aspect of the present invention concerns the use of a solubilizer for the stabilization of crude polyol produced from biomass.

The solubilizer is in particular a substance which is miscible with glycerin (1,2,3-propane triol), especially one which is homogeneously miscible, and preferably has a reduced tendency to phase separation in crude polyol. At least 5 wt. %, especially at least 10 wt. % of the solubilizer is preferably miscible with glycerin at room temperature.

"Biomass" or "renewable raw materials" means in the present case living as well as dead material. For example, this can be plants, animals, microorganisms, wood, leaves or straw. On the other hand, fossil energy sources such as coal, petroleum or natural gas, which have arisen from biomass in the geological past, are not considered to be biomass.

Polyols from fossil sources and polyols from biomass can be distinguished on the basis of their different fraction of $^{14}C$-isotopes by radiocarbon dating. Corresponding methods, such as the Libby counting tube method, liquid scintillation spectrometry, or accelerator mass spectrometric detection, are known to the skilled person.

A "polyol" in particular stands for an organic compound with at least 2 hydroxy groups. Preferred are compounds with precisely 2 or 3 hydroxy groups. Examples are ethylene glycol (1,2-ethane diol) or glycerin (1,2,3-propane triol).

A "polyol produced from biomass" in the present case can mean in particular a composition containing at least one polyol and one fraction of other organic and/or inorganic substances. The other substances are chemically different from the at least one polyol. For example, fatty acids, fatty acid esters, alcohols, water and/or sugar can be present as other substances. A fraction of additional substances preferably amounts to less than 50 wt. %, especially less than 20 wt. %, even more preferably less than 15 wt. %. In particular, a fraction of the other substances is 0.005-30 wt. %, preferably 5-20 wt. % or 5-10 wt. %.

"Stabilization" means in the present case especially a phase stabilization. The phase of the polyols from biomass should remain as stable as possible over time. In other words, the composition and the properties of the polyol phase should be stabilized or maintained. In particular, a phase separation or separation of another phase from the polyol phase should be reduced or prevented.

By "grinding" or "grinding process" is meant in particular a method in which a mean grain size of a solid or a mixture of different solids is reduced. This occurs for example in a mill during the grinding of clinker, optionally together with inert and/or active additives, such as gypsum, anhydrite, α-hemihydrate, β-hemihydrate, latent hydraulic binders, puzzolanic binders and/or inert fillers. The mentioned solids can also be ground up individually. Typically the solid or the mixture of different solids, especially a mineral binder, is ground down to a Blaine value of at least 500 $cm^2/g$, especially at least 1000 $cm^2/g$, preferably at least 2000 $cm^2/g$, even more preferably at least 2500 $cm^2/g$.

A "solid" in the present context is especially an inorganic and/or mineral solid. In particular, the solid is an inorganic substance for construction purposes, such as an ingredient of cement, mortar and/or concrete compositions. Preferably the solid is a mineral binder and/or an additive for a mineral binder. The solid can basically be present in coarse form, such as (unground) clinker, and/or already be partly ground.

A "mineral binder" is in particular a binder, especially an inorganic binder, which reacts in the presence of water in a hydration reaction to form solid hydrates or hydrate phases. This can be, for example, a hydraulic binder (such as cement or hydraulic lime), a latent hydraulic binder (such as slag or foundry sand), a puzzolanic binder (such as fly ash, trass or rice husk ash) and/or a nonhydraulic binder (gypsum or white lime). Mixtures of different binders are also possible.

Crude glycerin is preferred as the polyol from biomass. Advantageously the crude glycerin has a content of pure glycerin or 1,2,3-propane triol of at least 20 wt. %, preferably at least 50 wt. %, especially at least 75 wt. %, more preferably at least 80 wt. %. In particular, a glycerin fraction is 20-98 wt. %, especially 50-95 wt. %, particularly 50-90 wt. %.

Other organic and/or inorganic substances together have advantageously a fraction of less than 50 wt. %, especially 0.005-30 wt. %, preferably 5-20 wt. %. In particular, a fraction of inorganic alkaline metal salts is especially less than 20 wt. %, especially 1-15 wt. %, preferably 1-10 or 2-8 wt. %. The salts are in particular sodium chloride, sodium sulfide, potassium chloride, potassium sulfate or mixtures thereof. In particular, they are sodium chloride and/or sodium sulfate. Especially sodium chloride.

Especially suitable crude glycerin comes, for example, from biodiesel production. Biodiesel is produced, for example, by transesterification of rapeseed oil or soy oil with methanol. A by-product of this is crude glycerin, among others, which is advantageous in the present context on account of its composition. Furthermore, crude glycerin is available worldwide in large amounts from biodiesel production.

The crude polyol is preferably a crude glycerin with a content of glycerin or 1,2,3-propane triol as described above and a fraction of other organic and/or inorganic substances as described above. The crude glycerin or the other organic and/or inorganic substances in particular contain oil components as secondary components, especially oils, fatty acids and/or fatty acid esters, especially rapeseed oil and/or methyl ester of rapeseed oil.

The crude glycerin comprises, in particular, oil components as secondary components, especially oils, fatty acids and/or fatty acid esters which arise in the production of crude glycerin in biodiesel production or in the production of crude glycerin by transesterification of vegetable oils and/or fats, especially rapeseed oil and/or soy oil, with alcohols, preferably methanol.

In particular, the crude glycerin contains the oil secondary components, especially fatty acids and/or fatty acid esters, with a fraction of less than 50 wt. %, especially 0.005-30 wt. %, preferably 5-20 wt. % or 5-10 wt. %.

But essentially crude glycerin from other sources can also be used. Thus, crude glycerin arises, for example, also during soap production from coconut fat, olive oil, palm oil and animal fats such as tallow, lard, or fat from bones.

In particular, the solubilizer comprises an alkaline substance or consists of such.

The term "alkaline substance" in the present context stands in particular for a substance which when added to an aqueous solution is able to raise its pH value. Furthermore, the alkaline substance is miscible with glycerin, especially as described above.

Advantageously, the alkaline substance comprises an alkanolamine, a fatty amine and/or an alkaline hydroxide. In particular, the alkaline substance consists of one of the mentioned items or mixtures thereof.

Suitable alkanolamines are, for example, triethanolamine, diethanolamine, ethanolamine, diisopropanolamine, triisopropanolamine, diethanol-iso-propanolamine, ethanol-diisopropanolamine, N-methyl-diisopropanolamine, N,N,N',N'-tetrakis(2-hydroxyethyl)ethylene diamine, N,N,N',N'-tetrakis(2-hydroxy-propyl)ethylene diamine, N-methyldiethanolamine, N,N-dimethylethanolamine, N,N-diethylethanolamine. Especially suitable are diethanolamine, triisopropanolamine, diisopropanolamine, N-methyl-diisopropanolamine. Especially preferred are triethanolamine and/or triisopropanolamine.

The fatty amines used can be, e.g., octylamine, dodecylamine, tetradecylamine, coconut fatty amine, soybean fatty amine and/or stearyl amine.

Preferred alkaline hydroxides are, for example, sodium hydroxide and/or potassium hydroxide.

Especially preferably, the alkaline substance is an alkanolamine. This is surprising, since such substances generally do not constitute typical solubilizers. Triethanolamine and/or triisopropanolamine are especially advantageous.

Triethanolamine is especially preferred. Such substances enable on the one hand a good stabilization of the crude glycerin, on the other hand these substances are advantageous in regard to the use of the crude glycerin in grinding adjuvant compositions. This is because alkanolamines among other things can also act as grinding adjuvants and are relatively compatible with the substances generally present in grinding adjuvant compositions.

According to another preferred embodiment, the solubilizer comprises a glycol and/or a glycol ether or consists of such.

Possible glycols are, for example, ethylene glycol, diethylene glycol, triethylene glycol, tetraethylene glycol, propylene glycol, dipropylene glycol, and/or tripropylene glycol.

Possible glycol ethers are, for example, butylglycol, n-hexylglycol, methyldiglycol, ethyldiglycol, butyldiglycol, butyltriglycol, monophenylglycol, methoxypropanol, ethoxypropanol, dipropylene glycol methyl ether, tripropylene glycol methyl ether, propylene glycol-n-butyl ether, dipropylene glycol-n-butyl ether, tripropylene glycol-n-butyl ether and/or hexylene glycol.

Particularly suitable are monohydroxyglykol ethesr. Butyldiglycol has proven to be especially preferred. Butyldigycol is also known as 2-(2-butoxyethoxy)ethanol). With butyldiglycol, an especially effective stabilization of crude polyol has been observed. As has been shown, the solubilizer, especially the alkaline substance, is advantageously used with a fraction of 1-50 wt. %. Preferable is 1-30 wt. %, especially 1-9 wt. %, more preferably 5-9 wt. %. Each time the parts by weight are referred to the total weight of the composition, containing at least one polyol produced from biomass.

Especially preferably, the crude polyol is part of a grinding adjuvant composition or it is used as a grinding adjuvant or as a grinding adjuvant composition. In other words, the crude polyol stabilized by use of a solubilizer, especially an alkaline substance, can be used as a grinding adjuvant or as part of a grinding adjuvant composition for the grinding of solids, especially mineral binders and/or additives for mineral binders.

The grinding adjuvant composition contains in addition especially at least one additive chosen from the group consisting of polycarboxylates, glycols, amines, aminoalcohols, organic acids, ligninsulfonates, air pore formers, defoamers and/or retarders. With such additives or grinding adjuvant ingredients, the grinding adjuvant compositions can be specifically adapted to special requirements. This is especially in combination with solubilizers in the form of alkaline substances, especially alkanolamines.

Especially preferred are grinding adjuvant compositions which contain, besides the crude polyol, also at least one polycarboxylate. As described in WO 2005/123621 A1, such polymers themselves act as grinding adjuvants. By combination with crude polyol, an economical adapting of the grinding adjuvant composition to specific requirements can be achieved.

The at least one polycarboxylate is especially a comb polymer comprising a polycarboxylate backbone with polyether side chains attached to it. The side chains are bound in particular across ester, ether and/or amide groups to the polycarboxylate backbone.

Corresponding polycarboxylate ethers and production methods are disclosed for example in EP 1 138 697 B1 on page 7 line 20 to page 8 line 50, as well as its examples, or in EP 1 061 089 B1 on page 4, line 54 to page 5 line 38 and its examples. In one modification, as is described in EP 1 348 729 A1 on page 3 to page 5 and in its examples, the comb polymer can be produced in a solid state of aggregation. The disclosure of these cited patents is hereby incorporated in particular by reference.

Such comb polymers are also commercially marketed by Sika Schweiz AG under the brand name ViscoCrete®.

Another aspect of the invention involves a composition, especially a grinding adjuvant composition, comprising a crude polyol produced from biomass as well as a solubilizer. The solubilizer, especially an alkaline substance, and the crude polyol are defined as above. The grinding adjuvant composition is especially suitable for the grinding of solids, such as mineral binders.

In particular, the solubilizer, especially the alkaline substance, is present in a quantity of 1-9 wt. %, preferably 2-7 wt. %, in terms of the total weight of the grinding adjuvant composition.

Further, the composition can contain in particular the additives already mentioned above.

Especially preferred is a grinding adjuvant composition containing or consisting of:
 a) 5-95 wt. %, especially 10-80 wt. %, particularly 20-50 wt. %, of crude polyol, especially in the form of crude glycerin
 b) 0.1-9 wt. %, especially 1-7 wt. %, of the alkaline substance, preferably an alkanolamine
 c) 0-40 wt. % of a polycarboxylate
 d) 0-60 wt. % of a glycol
 e) 0-10 wt. % of an organic acid
 f) the remainder up to 100 wt. % water.

Especially advantageous are compositions containing 5-40 wt. %, especially 10-30 wt. %, of the polycarboxylate.

Glycol in particular has a fraction of 5-50 wt. %, especially 25-40 wt. %.

A fraction of the organic acid of 1-10 wt. %, especially 2-6 wt. %, has proven to be optimal.

Another aspect of the invention concerns a binder composition containing a mineral binder as well as a grinding adjuvant composition. The mineral binder and the grinding adjuvant composition are present in particular as described above. The grinding adjuvant composition has, in particular, a fraction of 0.001-1 wt. % in terms of the mineral binder.

Furthermore, the invention pertains to a method of grinding of a solid, especially a mineral binder, wherein the solid is ground with a grinding adjuvant composition. The grinding adjuvant composition is present in particular with a fraction of 0.001-1.0 wt. % in terms of the solid being ground.

Further advantageous embodiments and combination of features of the invention will emerge from the following detailed specification and the totality of the patent claims.

SAMPLE EMBODIMENTS

1. Stabilization of Crude Glycerin

In a vessel, crude glycerin (Wetterauer Agrarservice GmbH—glycerin content: 80%) from biodiesel production was reacted with the quantities of alkaline substances indicated in table 1 and stirred for 5 minutes. The samples were then allowed to stand and the duration (separation time) until formation of a visible separation phase was determined. Table 1 gives a survey of the samples produced and their properties.

TABLE 1

| Sample | Alkaline substance (fraction in wt. %) | Separation time |
| --- | --- | --- |
| A | Triethanolamine (5.0%) | >6 months |
| B | Triethanolamine (15%) | >6 months |
| C | Triethanolamine (50%) | >6 months |
| D | Triisopropanolamine (15%) | >6 months |
| E | Butyldiglycol (15%) | >6 months |
| V | None | 1 week |

It is evident from table 1 that alkaline substances are able to stabilize the crude glycerin for a long time. Samples A-E show even after 6 months no visible phase separation. This in contrast with the unstabilized comparison sample V, on which a separation layer formed already after 4 weeks.

2. Grinding Adjuvant Composition

Furthermore, a grinding adjuvant composition MZ was prepared with the components indicated in table 2. For this, the individual components were blended together. The polycarboxylate ether used was Viscocrete VC 1020X (available from Sika Schweiz AG).

TABLE 2

| Component | Fraction [wt. %] |
| --- | --- |
| Crude glycerin | 30 |
| Triethanolamine | 10 |
| Polycarboxylate ether | 20 |
| Diethylene glycol | 10 |
| Acetic acid (60% in $H_2O$) | 5 |
| Water | 25 |

Composition MZ proved to be stable in storage for at least 6 months. No phase separation was observed during this time.

3. Grinding Tests

Samples A-D and the grinding adjuvant composition MZ were used as additives during the grinding of cement clinker as a grinding adjuvant on a laboratory grinding mill. Each time, 300 g of a cement clinker (Vigier) was ground on the laboratory ball mill under identical conditions with 0.02 wt. % of the particular additive (quantity of sample A-D or grinding adjuvant composition MZ in terms of cement clinker). Test M0 is a reference sample without additive. The conditions such as the grinding time were kept constant for all grinding tests.

After the grinding was over, the Blaine fineness was determined per standard EN 196-6 and the sifting residue of particles over 32 μm (in wt. % in terms of all particles) was determined per standard EN 196-6 (May 2010) with a 32 μm screen. The results were further verified by laser granulometry.

Table 3 shows a summary of the grinding tests performed and the corresponding results.

TABLE 3

| | Test | | | | | |
| --- | --- | --- | --- | --- | --- | --- |
| | M0 | M1 | M2 | M3 | M4 | M5 |
| Additive | — | A | B | C | D | MZ |
| Fineness [cm$^2$/g] | 1745 | 2215 | 2275 | 2460 | 2315 | 2550 |
| Sifting residue >32 μm [wt. %] | 45.3 | 38.1 | 36.2 | 33.1 | 35.8 | 32.2 |

It is evident from table 3 that stabilized crude glycerin as well as the grinding adjuvant composition MZ based on it can be used advantageously as a grinding adjuvant. No clogging or fouling of pumps and pipelines or disturbances during grinding or resinification was observed.

However, the above-described embodiments are to be taken only as illustrative examples, which can be modified at will in the scope of the invention.

The invention claimed is:

1. A composition comprising a crude polyol produced from biomass, wherein the composition contains the following in wt. % in terms of the total weight of the composition:
    a) 10-80 wt. % of the crude polyol in the form of crude glycerin,
    b) 1-9 wt. % of the solubilizer, where the solubilizer is an alkanolamine,
    c) 5-40 wt. % of a polycarboxylate,
    d) 5-50 wt. % of a glycol,
    e) 1-10 wt. % of an organic acid,
    f) the remainder up to 100 wt. % water.

2. A binder composition containing a mineral binder as well as a composition according to claim 1.

3. A method for grinding a solid, the method comprising: grinding the solid with a composition according to claim 1.

4. The composition according to claim 1, wherein the weight percent of the solubilizer is 2-7 wt. %.

5. The composition according to claim 1, wherein the alkaline substance is triethanolamine and/or triisopropanolamine.

6. The composition according to claim 1, wherein the solubilizer further comprises glycol and/or a glycol ether.

7. The composition according to claim 1, wherein the solubilizer further comprises a monohydroxyglycol ether.

8. The composition according to claim 1, wherein the solubilizer further comprises butyldiglycol.

9. The composition according to claim 1, wherein
   the polycarboxylate is a comb polymer comprising a polycarboxylate backbone with polyether side chains attached to the backbone, and
   the side chains of the comb polymer are bound to the polycarboxylate backbone by ester, ether and/or amide groups.

10. The composition according to claim 1, wherein the composition contains:
    10-30 wt. % of the polycarboxylate;
    25-40 wt. % of the glycol; and
    2-6 wt. % of the organic acid.

11. A method comprising:
    stabilizing crude polyol produced from biomass by preparing the composition of claim 1 containing the following in wt. % in terms of the total weight of the composition:
    a) 10-80 wt. % of the crude polyol in the form of crude glycerin,
    b) 1-9 wt. % of the solubilizer, where the solubilizer is an alkanolamine,
    c) 5-40 wt. % of a polycarboxylate,
    d) 5-50 wt. % of a glycol,
    e) 1-10 wt. % of an organic acid,
    f) the remainder up to 100 wt. % water.

12. The method according to claim 11, wherein the crude polyol further comprises a fraction of pure polyol or 1,2,3-propane triol.

13. The method according to claim 11, wherein the crude polyol consists of crude glycerin.

14. The method according to claim 13, wherein the crude glycerin comes from biodiesel production.

15. The method according to claim 11, wherein the solubilizer further comprises a glycol and/or a glycolether.

16. The method according claim 11, wherein
    the crude polyol is part of a grinding adjuvant composition or
    the crude polyol is stabilized while being used as a grinding adjuvant or a grinding adjuvant composition.

17. The method according to claim 11, wherein the crude polyol is part of a grinding adjuvant composition that further comprises at least one additive selected from the group consisting of amines, aminoalkohols, ligninsulfonates, air pore formers, defoamers and retarders.

\* \* \* \* \*